(12) United States Patent
Suzuki et al.

(10) Patent No.: US 6,814,952 B2
(45) Date of Patent: Nov. 9, 2004

(54) DIAGNOSTIC IMAGING AGENT USEFUL FOR SELECTING A THERAPY FOR CANCEROUS BONE METASTASIS

(75) Inventors: Kazuko Horiuchi Suzuki, Kyoto (JP); Hideo Saji, Kyoto (JP); Akira Yokoyama, Shiga (JP)

(73) Assignee: Nihon Medi-Physics Co., Ltd., Hyogo (JP)

( * ) Notice: Subject to any disclaimer, the term of this patent is extended or adjusted under 35 U.S.C. 154(b) by 0 days.

(21) Appl. No.: 09/953,931

(22) Filed: Sep. 18, 2001

(65) Prior Publication Data

US 2002/0131934 A1 Sep. 19, 2002

(30) Foreign Application Priority Data

Mar. 16, 2001 (JP) ........................................ 2001-077310

(51) Int. Cl.$^7$ .............................................. A61K 49/00
(52) U.S. Cl. .................. 424/9.1; 424/1.11; 424/1.65; 514/1; 514/706; 514/708
(58) Field of Search ............................... 424/1.11, 1.65, 424/9.1, 9.3, 9.4, 9.5, 9.6, 9.7, 9.8; 534/7, 10–16; 514/1, 706, 708

(56) References Cited

U.S. PATENT DOCUMENTS 5,874,573 A * 2/1999 Winchell et al. ............ 540/465

FOREIGN PATENT DOCUMENTS

JP          56-7725 A          1/1981

OTHER PUBLICATIONS

A. Konno et al., Jpn. J. Nucl. Med. 37:576 (2000).
K. Horiuchi et al., Jpn. J. Nucl. Med. 37:576 (2000).
H. Kobayashi et al., Eur. J. Nucl. Med. 22:559–562 (1995).
I. Yomoda et al., Jpn. J. Nucl Med. 24:77–82 (1997).
H. Kobayashi et al., Clin. Nucl. Med. 20:361–364 (1995).
J. Banzo et al., Eur. J. Nucl. Med. 20:202 (1990).
A.S.K. Lam et al., Nucl. Med. Comun. 18:907–914 (1997).
M. Sahin et al., Nucl. Med. Comun. 21:251–258 (2000).
A.S.K. Lam et al., Eur. J. Nucl. Med. 23:1575–1582 (1996).
K. Horiuchi et al., Nucl. Med. Biol. 26:771–779 (1999).

* cited by examiner

Primary Examiner—Dameron L. Jones
(74) Attorney, Agent, or Firm—Fitch, Even, Tabin & Flannery

(57) ABSTRACT

A diagnostic imaging agent useful for selection of a therapy for cancerous bone metastasis is provided, which comprises $^{99m}$Tc(V)-dimercaptosuccinic acid as an effective ingredient. The agent is administered to a patient, and a scintigram is taken. This is especially useful for identifying osteoclastic type or mixed type bone metastasis or for identifying a disease in which the bone resorption due to osteoclast is enhanced, and thus allows a proper selection of therapies for such diseases.

9 Claims, 13 Drawing Sheets

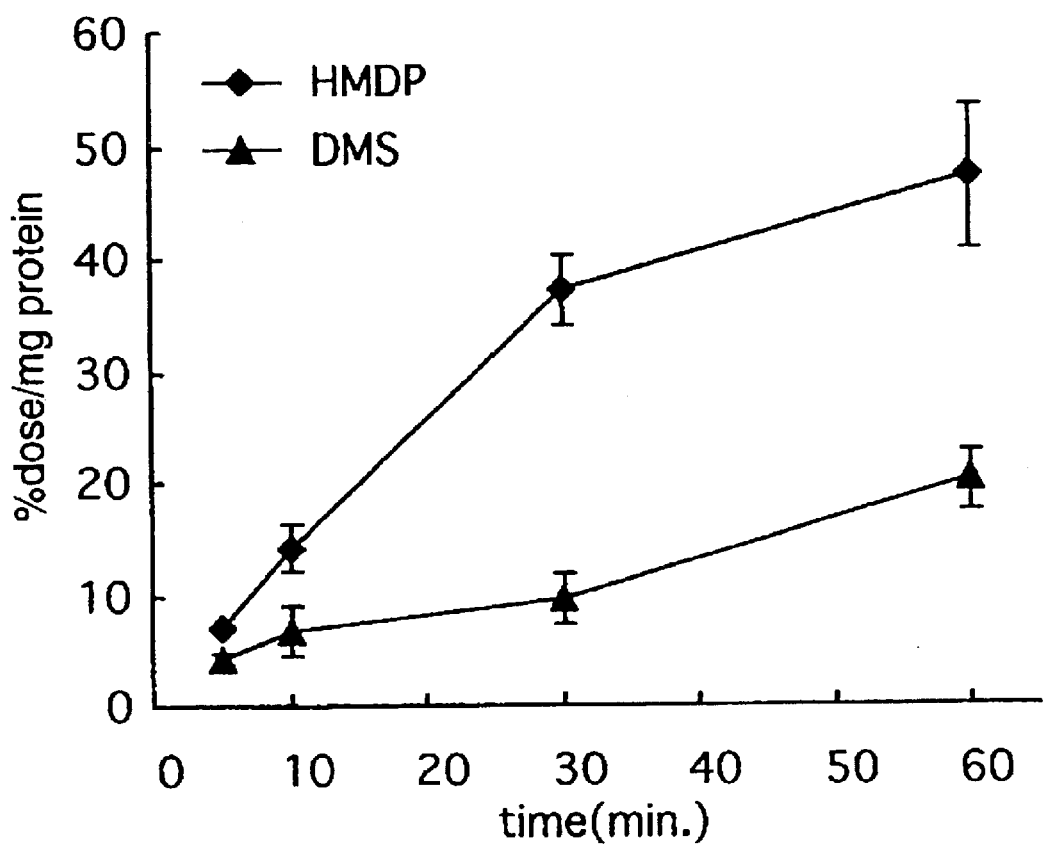
F I G. 1

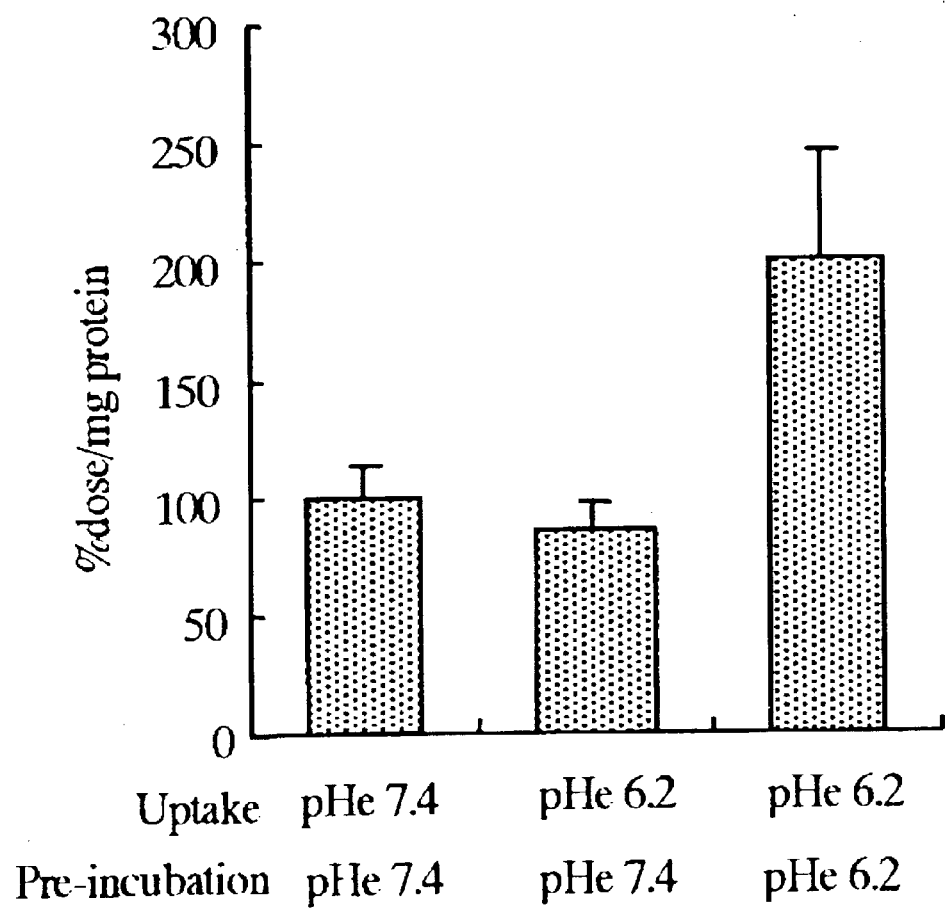
F I G. 5

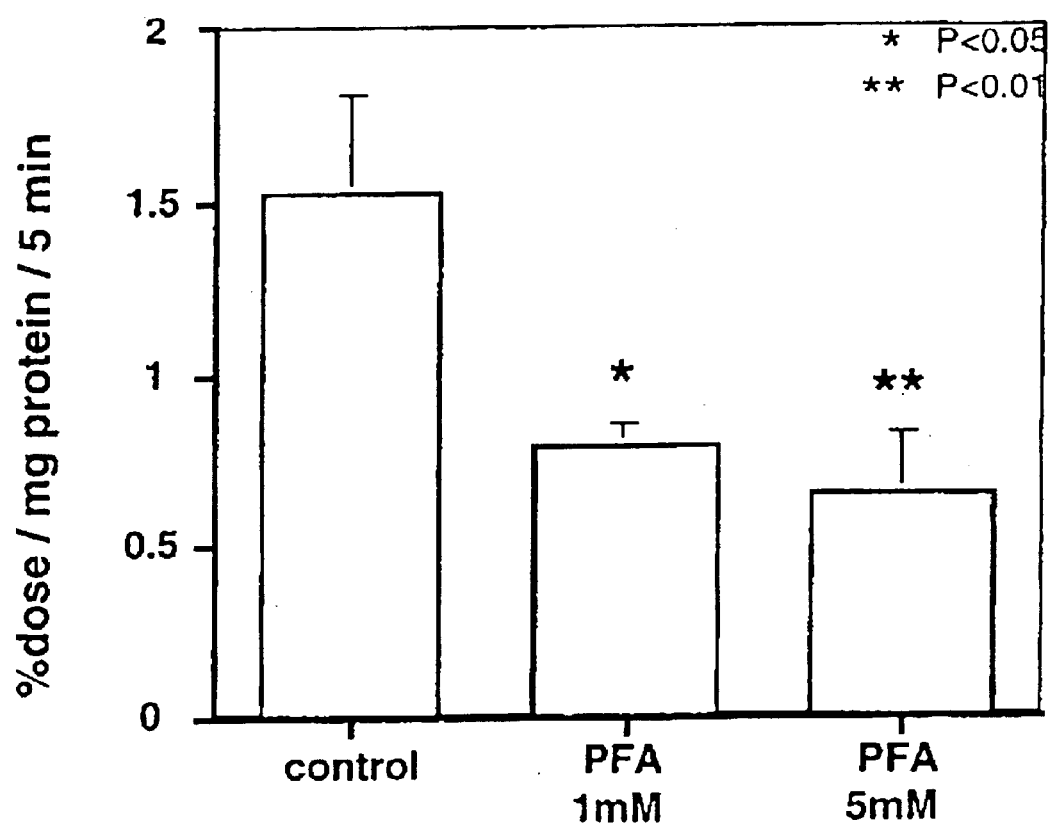
F I G. 7

DIAGNOSTIC IMAGING AGENT USEFUL FOR SELECTING A THERAPY FOR CANCEROUS BONE METASTASIS

BACKGROUND OF THE INVENTION

1. Field of the Invention

The present invention relates to the use of $^{99m}$Tc(V)-dimercaptosuccinic acid for detecting cancerous bone metastasis of the osteoclastic or mixed type by means of bone scintigraphy, and facilitating selection of a therapy for the cancerous bone metastasis.

2. Description of Related Art Including Information Disclosed under 37 CFR 1.97 and 1.98

Whether cancerous bone metastasis has occurred is an important factor that affects prognosis, and also influences the therapeutic plan for the primary lesion. Furthermore, since options of therapies for bone metastasis and accompanying symptoms are increasing, diagnosis of presence or absence, or spread of bone metastasis plays an important role in deciding a therapeutic plan. Bone metastasis can be seen more or less in every cancer. The diagnosis of bone metastasis would be of particular importance in breast cancer, prostatic cancer, lung cancer, thyroid cancer and renal cancer since these cancers are generally considered higher in risk of bone metastasis than other cancers.

Bone metastasis can be pathologically classified into four types: osteoblastic type, osteoclastic type, mixed type in which the aforementioned two types are mixed together, and inter-trabecular type in which neither osteoblastic nature nor osteoclastic nature is exhibited. Among the cancers high in the risk of bone metastasis, it is likely that prostatic cancer causes the osteoblastic type, renal cancer and thyroid cancer causes the osteoclastic type, lung cancer causes both the osteoclastic and the mixed types, and breast cancer causes the mixed type. Among the four types, the osteoclastic type is characterized by bone resorption due to growth of osteoclastic cells, and is likely to result in bone fracture. For this reason, the osteoclastic type of bone metastasis is said to have a significantly higher incidence of pains than other types. Among the patients of breast cancer with bone metastasis, it is said that patients of the osteoblastic type survive the longest, being followed by patients of mixed type and osteoclastic type, in this order. So, the identification of metastasis type is also considered important.

Bone scintigraphy is generally used to examine the presence or absence of bone metastasis in cancer patients. Usually, a $^{99m}$Tc-labelled bisphosphonate ($^{99m}$Tc-BP) such as $^{99m}$Tc-MDP (methylene diphosphonate), $^{99m}$Tc-EHDP (ethane hydroxy-diphosphonate) or $^{99m}$Tc-HMDP (hydroxymethylene diphosphonate) is intravenously injected as a diagnostic imaging agent, and then scintigrams are taken. Mechanism of bone accumulation of the $^{99m}$Tc-BP is still unclear, but it is found that the $^{99m}$Tc-BP highly accumulates in osteoblastic lesions. So, the $^{99m}$Tc-BP is useful for detecting the osteoblastic type bone metastasis. However, the $^{99m}$Tc-BP does not appear to depict lesions of osteoclastic type bone metastasis as positive images, and this is a problem.

On the other hand, as for $^{99m}$Tc-dimercaptosuccinic acid ($^{99m}$Tc-DMS), the trivalent $^{99m}$Tc-DMS is well known as a diagnostic imaging agent for kidney, while pentavalent $^{99m}$Tc(V)-DMS is reported to accumulate in tumor lesions such as of thyroid carcinoma (MTC), osteosarcoma, and benign and malignant tumors of various soft tissues. JP-A-56-7725 proposes the use of $^{99m}$Tc(V)-DMS as a tumor scanning agent. Furthermore, it is also reported that $^{99m}$Tc(V)-DMS depicts lesions of bone metastasis caused by various cancers as positive images.

As described above, $^{99m}$Tc(V)-DMS is a polynuclear complex having a nature of accumulating in both cancers and bones. The accumulation in cancers is presumed to depend on pH values, but no mechanism of the accumulation in bones has been known even though there are clinical reports that the $^{99m}$Tc(V)-DMS would accumulate in lesions of osteoclastic type metastasis.

Meanwhile, bone fractures involved in the bone metastasis of tumors are considered to include those caused directly by protease secreted from tumor cells and those caused by way of activated osteoclast. In recent years, it has been clarified that bone resorption is inhibited by bisphosphonate compounds such as pamidronate, clodronate, etidronate, tiludronate and alendronate, and that these compounds would be effective for preventing bone fractures associated with osteoporosis and tumorous bone metastasis. Mechanism of the inhibitory action on bone resorption has not yet been sufficiently clarified, but it is said that the inhibitory action results from bisphosphonate compounds that act directly or indirectly on osteoclast, thereby inactivating and decreasing osteoclast. Therefore, if any diagnostic method using any compound specifically taken up by osteoclast is established, it will become possible to accurately select patients who are suited to therapy targeted at osteoclast by use of the recently developed bisphosphonate compounds.

Under the above-mentioned circumstances, the object of present invention is to allow a precise diagnostic imaging of cancerous osteoclastic type or mixed type bone metastasis using a compound capable of being specifically taken up by osteoclast, thereby enabling an appropriate selection of a therapy based on the diagnosis.

SUMMARY OF THE INVENTION

In order to achieve the above-mentioned object, the inventors have intensively studied on the mechanism of $^{99m}$Tc(V)-DMS accumulation in the lesions of bone metastasis, and as a result, have found that while the $^{99m}$Tc-BP used as a conventional diagnostic imaging agent is remarkably taken up by osteoblast but is hardly taken up by osteoclast, $^{99m}$Tc(V)-DMS shows the following characters (1)–(5): (1) $^{99m}$Tc(V)-DMS is less taken up by osteoblast than $^{99m}$Tc-BP, but is taken up by osteoclast in an especially large amount. (2) The amount of the $^{99m}$Tc(V)-DMS taken up by osteoclast remarkably increases at low pH values. (3) The phenomenon of the above (2) is presumed to have relation with activation of function of the osteoclast in an acidic environment. (4) $^{99m}$Tc(V)-DMS shows a behavior similar to phosphate anion when taken up by osteoclast, and it is taken up by osteoclast through $Na^+$-dependent phosphate transporter that relates to the transport of inorganic phosphate to osteoclast. (5) $^{99m}$Tc(V)-DMS shows a distribution in vivo that corresponds to the distribution of osteoclast, and thus is preferentially taken up by osteoclast rather than osteoblast. On the basis of these evidences, the present invention has been completed.

According to the present invention, provided is a diagnostic imaging agent useful for selecting a therapy for cancerous bone metastasis, comprising $^{99m}$Tc(V)-dimercaptosuccinic acid as an effective ingredient. Cancerous bone metastases include those of the osteoclastic or mixed type which accompanies localization and activity rise of osteoclast, and those of the osteoblastic or inter-trabecular type which is considered to receive no or little contribution of osteoclast. Since $^{99m}$Tc(V)-dimercaptosuccinic acid is highly specific to osteoclast, it allows the osteoclastic type or mixed type bone metastasis to be accurately identified, and facilitates the decision as to whether or not a therapy targeted at osteoclast should be applied.

DETAILED DESCRIPTION OF THE INVENTION

There is no limitation in kinds of the therapy targeted at osteoclast as long as they are expected to give a therapeutic effect in a way that directly or indirectly acts on osteoclast and thereby inhibits bone resorption or palliates bone pain. Typically, such a therapy includes one using a bisphosphonate compound.

The bisphosphonate compound means germinal bisphosphonates having a P-C-P skeleton structure, and includes many therapeutic agents that are commercially available or clinically being developed, such as etidronate, clodronate, pamidronate, alendronate, ibandronate, incadronate, olpadronate, zoledronate, tiludronate, neridronate, risedronate, YH592 and EB-1053.

Besides, a therapy is practiced in which $^{89}$SrCl$_2$ or another compound having affinity with bones is intravenously administered, and then a lesion of a cancerous bone metastasis is irradiated in vivo in order to efficiently palliate the pain involved in the bone metastasis. While $^{89}$SrCl$_2$ can highly accumulate in lesions of osteoblastic type bone metastasis, it is predicted that $^{186}$Re or $^{188}$Re-labeled dimercaptosuccinic acid attempted for clinical application similarly to $^{89}$SrCl$_2$ can highly accumulate in lesions of osteoclastic type or mixed type bone metastasis where osteoclast is localized. Therefore, the present diagnostic imaging using $^{99m}$Tc(V)-DMS is useful for the selection of these bone pain palliation agents.

According to another aspect of the present invention, there is provided a method of diagnosis for localization of osteoclast, which comprises administering a patient with a diagnostic imaging agent that contains $^{99m}$Tc(V)-dimercaptosuccinic acid as an effective ingredient, and then taking a scintigram, whereby osteoclast are located.

Diagnosis for scrutinizing the localization of osteoclast can be applied to the diseases in which bone resorption caused by osteoclast increases, and the diseases typically covered by the diagnosis are osteoporosis and osteoclastic type or mixed type cancerous bone metastases.

In both cases of the above selection of therapy and the above diagnosis of localization, the diagnostic imaging agent containing $^{99m}$Tc(V)-dimercaptosuccinic acid as an active ingredient can be used alone to achieve the object, but it may also be used in combination with a diagnostic agent containing $^{99}$Tc-BP so as to more accurately evaluate participation of osteoclast.

The $^{99m}$Tc(V)-dimercaptosuccinic acid used in the present invention can be obtained by mixing a $^{99m}$Tc pertechnetate solution with a solution that contains dimercaptosuccinic acid and a reducing agent such as stannous chloride with adjustment to alkaline pH using a sodium hydrogen carbonate buffer or the like. For example, as disclosed in H. Kobayashi et al., Eur. J. Nuc. Med. 22: 559–562 (1995), it can readily be produced by adding a sodium hydrogen carbonate buffer to a commercially available renal scintigraphic preparation ($^{99m}$Tc (III)-DMS) kit for adjustment to alkaline pH, and then mixing the resultant solution with a $^{99m}$Tc pertechnetate solution. In this instance, a small amount of oxygen may be allowed to oxidize $^{99m}$Tc(III)-DMS and excessive stannous chloride so that radiochemical purity is improved. However, drugs should be prepared using a special kit for it, and for this purpose, a labeling kit specifically designed for $^{99m}$Tc(V)-DMS disclosed in I. Yomoda et al., Jpn. J. Nucl. Med. (Kaku Igaku), 24: 77–82 (1987) is available. This kit has dimercaptosuccinic acid, stannous chloride and others contained as freeze-dried in a sealed vial, and $^{99m}$Tc(V)-DMS can be prepared by adding a $^{99m}$Tc pertechnetate solution containing a small amount of sodium hydrogen carbonate buffer to the vial.

Usually, the thus-produced $^{99m}$Tc(V)-DMS preparation is intravenously administered by 100 MBq to 1500 MBq, preferably 200 MBq to 1000 MBq, more preferably 350 MBq to 750 MBq. The dosage may be varied depending upon the weight and the like of a patient.

Within a period of 30 minutes to five hours, preferably 1 hour to 4 hours, more preferably 2 hours 3 hours after administration, anterior and posterior images or divisional images of the whole body, and as required, spot images or tomograms (single-photon-emission computed tomographic (SPECT) images) of specific regions are taken as scintigrams. Based on the thus-obtained scintigrams, diagnosis and appropriate selection of therapy can be made.

According to the present invention, the presence or absence of active osteoclast or osteoclastic lesions can be identified, and thus it becomes possible to accurately determine the applicability of therapies targeted at osteoclast. For this reasons, misdirected therapies will decrease, and a great advantage in terms of medical economy will be provided. Also, patient's choices of effective therapies will increase, and in turn the risk of losing chances of receiving effective therapies due to sustained application of ineffective therapies will decrease.

BRIEF DESCRIPTION OF THE SEVERAL VIEWS OF THE DRAWING

FIG. 1 is a graph showing the time course of cellular uptake of $^{99m}$Tc(V)-DMS (▲) and $^{99m}$Tc-HMDP (♦) by osteoblast.

FIG. 5 is a graph showing the effect of incubation modality on the cellular uptake of $^{99m}$Tc(V)-DMS by osteoclast.

FIG. 7 is a graph showing the effect of sodium ion-dependent phosphate transporter inhibitor on the cellular uptake of $^{99m}$Tc(V)-DMS by osteoclast.

DESCRIPTION OF THE PREFERRED EMBODIMENT

EXAMPLES

Figure 2:
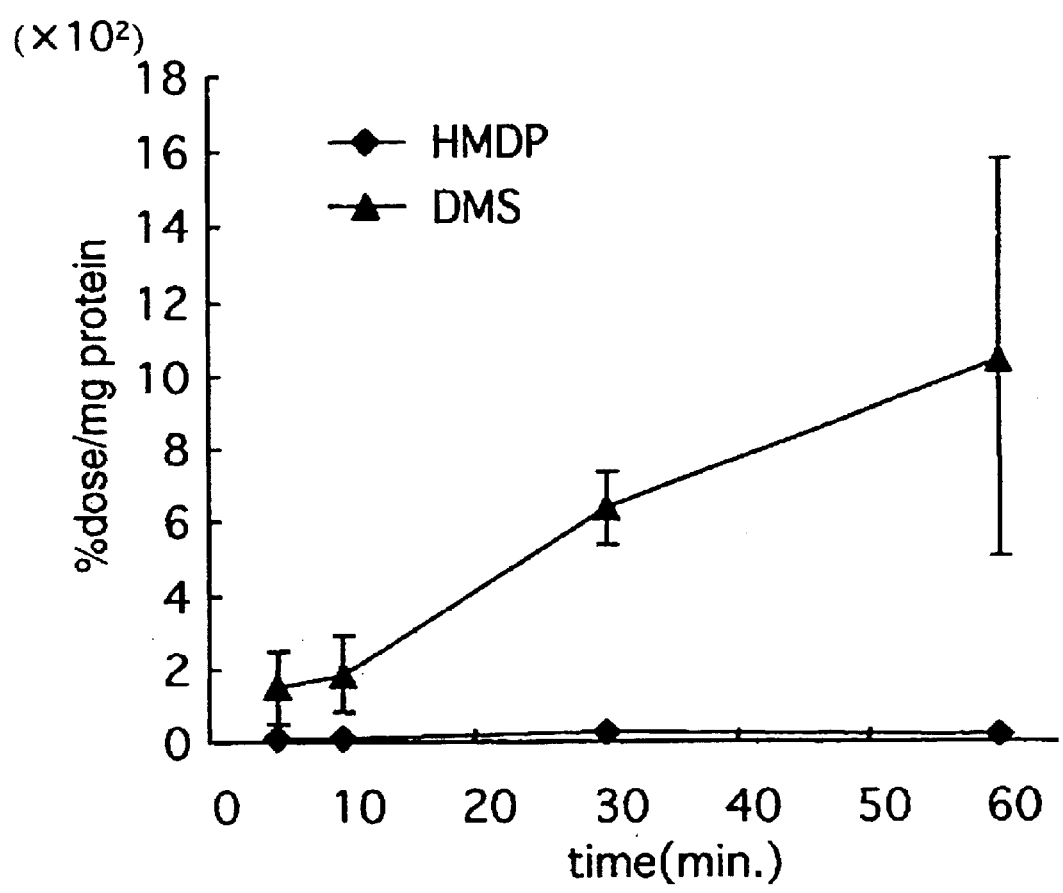
FIG. 2 is a graph showing the time course of cellular uptake of $^{99m}$Tc(V)-DMS (▲) and $^{99m}$Tc-HMDP (♦) by osteoclast.

The present invention will be described below in more detail with reference to examples, but is not limited thereto or thereby.

Example 1
Preparation of $^{99m}$Tc(V)-DMS

A $^{99m}$Tc pertechnetate solution (18.5 to 370 MBq) eluted from a technetium generator was added to an aqueous solution containing 1.36 mg of dimercaptosuccinic acid, and 0.285 mL of 7% sodium hydrogen carbonate solution was further added thereto, to obtain 2.5 ml of a solution in total. Then, 0.02 mL of 0.01M stannous chloride solution prepared using 0.1M hydrochloric acid solution was added thereto, and the mixture was allowed to stand at room temperature for 15 minutes. This series of operations was performed under nitrogen gas atmosphere. Radiochemical purity of the $^{99m}$Tc(V)-DMS thus obtained was measured by means of thin layer chromatography using a n-butanol/acetic acid/water mixed solution (3:2:3) or acetone as a developing solvent on a silica gel thin layer plate. The radiochemical purity was 93 to 95%.

$^{99m}$Tc-HMDP used as a control in the following experiments was prepared by adding the $^{99m}$Tc pertechnetate solution eluted from the technetium generator to HMDP of a commercially available labeling kit.

Example 2
Uptake of $^{99m}$Tc(V)-DMS by Osteoclast and Osteoblast
Culture of Cells Osteoblast was isolated from the parietal bone of a newborn mouse by means of stepwise enzyme digestion according to a method described by Takahashi et al. (Takahashi et al., Endocrinology, 123: 2600–2602 (1988)), and cultured using α-MEM (10% fetal calf serum) for 6 to 8 days for use in the following experiments. Furthermore, osteoclast was obtained by co-culturing osteoblastic cells and bone marrow cells for 6 to 8 days using α-MEM (10% fetal calf serum, $10^{-8}$ M vitamin $D_3$, pH 6.2) on a collagen-coated dish according to a method described by Takahashi et al. (Takahashi et al., Endocrinology, 122: 1373–1382 (1988)). The osteoclast was identified by means of tartaric acid-resistant acidic phosphatase dyeing.

Experiment of uptake by cells: The osteoblast or the co-cultured osteoclast was isolated using 35% Percoll and incubated using α-MEM (10% fetal calf serum) at 37° C. in an atmosphere of 5% $CO_2$ and 95% air for 3 hours. The incubated cells were washed with an incubation buffer of pH 7.4 (10 mM HEPES, 5 mM glucose, 150 mM NaCl, 5 mM KCl, 1.8 mM $MgSO_4$, 1 mM $CaCl_2$) three times, and pre-incubated using the same buffer at 37° C. for 30 minutes. Then, the cells in incubation buffer containing $^{99m}$Tc(V)-DMS at a concentration of 129.5 kBq/mL were allowed to infiltrate, and washed with the ice-cooled incubation buffer three times, 5, 10, 30 and 60 minutes later. Then, the cells were lysed with 0.2N NaOH, and radioactivity taken up by the cells was measured using a gamma counter. After completion of the radioactivity measurement, the amount of proteins contained in the cell lysate was measured using BCA Protein Assay Kit (produced by Pierce), and the $^{99m}$Tc-DMS uptake per unit protein mass (% dose/mg protein) was obtained. As to $^{99m}$Tc-HMDP, a similar experiment was carried out for comparison. The results are shown in FIGS. 1 and 2.

From the comparison between FIGS. 1 and 2, it can be seen that $^{99m}$Tc(V)-DMS is taken up by osteoclastic cells in an especially large amount (FIG. 2) while it is taken up by osteoblastic cells in an amount smaller than $^{99m}$Tc-HMDP (FIG. 1).

Example 3
Effect of pH on the Uptake of $^{99m}$Tc(V)-DMS by Osteoclast and Osteoblast In the method described in Example 2, the pH of the incubation buffer was set at 6.2, 6.6, 7.0, 7.4, 7.8 or 8.2, and the incubation time for $^{99m}$Tc(V)-DMS uptake was set at 10 minutes, to examine the effect of pH on the uptake of $^{99m}$Tc(V)-DMS by osteoclast and osteoblast. A similar experiment was carried out for $^{99m}$Tc-HMDP for comparison. The results are shown in FIGS. 3 and 4.

Figure 3:
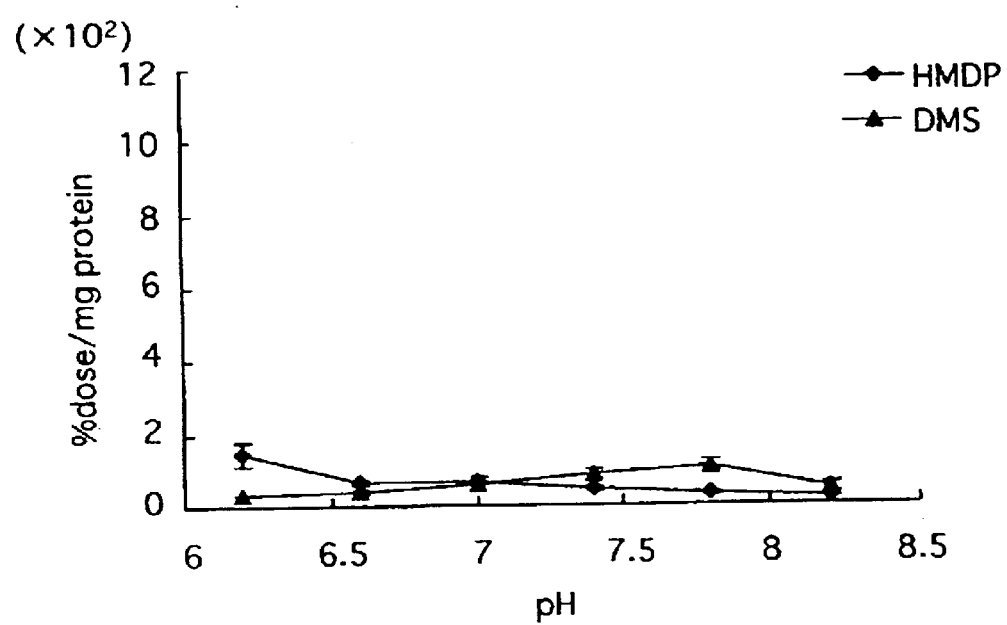
FIG. 3 is a graph showing the effect of pH on the cellular uptake of $^{99m}$Tc(V)-DMS (▲) and $^{99m}$Tc-HMDP (♦) by osteoblast.
Figure 4:
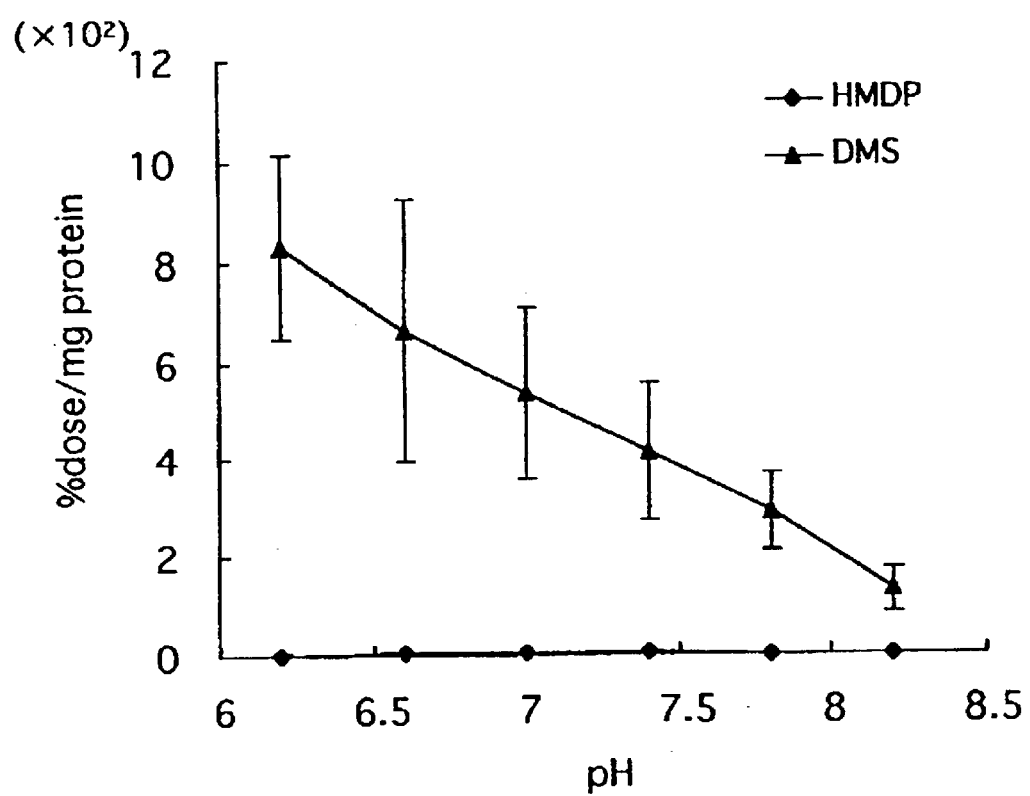
FIG. 4 is a graph showing the effect of pH on the cellular uptake of $^{99m}$Tc(V)-DMS (▲) and $^{99m}$Tc-HMDP (♦) by osteoclast.

From the comparison between FIGS. 3 and 4, it can be seen that the uptake by osteoblast does not show any significant difference between $^{99m}$Tc(V)-DMS and $^{99m}$Tc-HMDP irrespectively of pH (FIG. 3), but that the uptake of $^{99m}$Tc(V)-DMS into osteoclast remarkably increases as the pH value decreases (FIG. 4).

Example 4
Effect Osteoblast of Extracellular pH on the Uptake of $^{99m}$Tc(V)-DMS by Osteoclast In the method described in Example 2, an incubation buffer of pH 7.4 was used for pre-incubation, and an incubation buffer of pH 6.2 was used for the buffer containing $^{99m}$Tc(V)-DMS, while the incubation time for $^{99m}$Tc(V)-DMS uptake was set at 10 minutes, to measure the uptake of $^{99m}$Tc(V)-DMS into osteoclast.

Compared with the cases where pH values of the buffers for both pre-incubation and $^{99m}$Tc(V)-DMS uptake were 6.2 and 7.4 as shown in Example 3, effect of extracellular pH (pHe) on the uptake was examined. The results are shown in FIG. 5.

From FIG. 5, it can be seen that when the pH values of the buffers for both pre-incubation and uptake by osteoclast are 6.2, the uptake of $^{99m}$Tc(V)-DMS rises. Furthermore, it can also be seen that in order to achieve higher uptake, the osteoclast must be placed in an acidic environment for a certain period of time. It is reported that osteoclast is generally activated in an acidic environment (T. Tamura et al., J. Bone Miner. Res. 8: 953–960 (1993)). So, it is considered that the increase of uptake at a low pH has relation with activation of osteoclast.

Example 5
Participation of Sodium Ion-dependent Phosphate Transporter in the Uptake of $^{99m}$Tc(V)-DMS by Osteoclast In the method described in Example 2, an incubation buffer of pH 7.4 was used for pre-incubation, and the buffer containing $^{99m}$Tc(V)-DMS was an incubation buffer of pH 7.4 with the phosphate anion concentration ([Pi]) adjusted to 0 mM, 0.05 mM, 0.1 mM, 0.5 mM, 1.0 mM or 5.0 mM, while the incubation time was set at 5 minutes, to measure the uptake of $^{99m}$Tc(V)-DMS by osteoclast.

Figure 6:
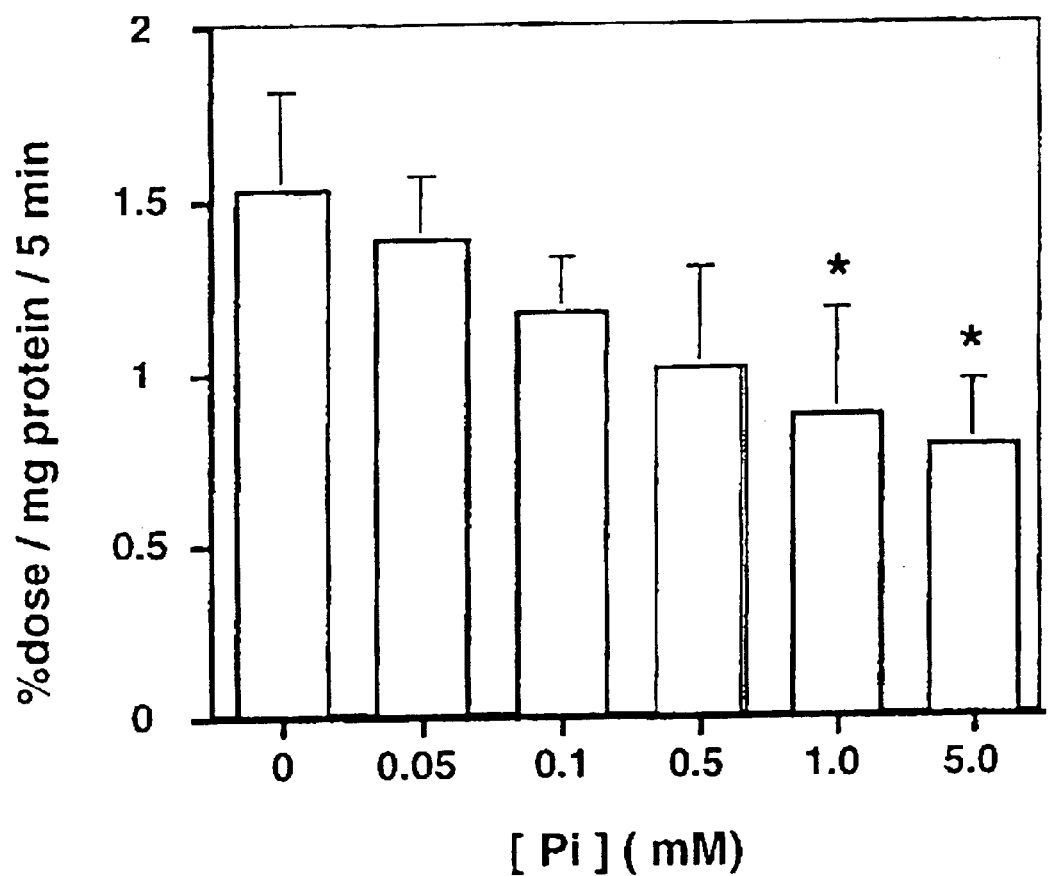
FIG. 6 is a graph showing the effect of phosphate anion concentration on the cellular uptake of $^{99m}$Tc(V)-DMS by osteoclast.

Furthermore, a similar experiment was carried out except that the buffer containing $^{99m}$Tc(V)-DMS was an incubation buffer of pH 7.4 containing 1 mM or 5 mM of phosphonoformic acid (PFA) which was a sodium ion-dependent phosphate transporter inhibitor. The results are shown in FIGS. 6 and 7.

Figure 8:
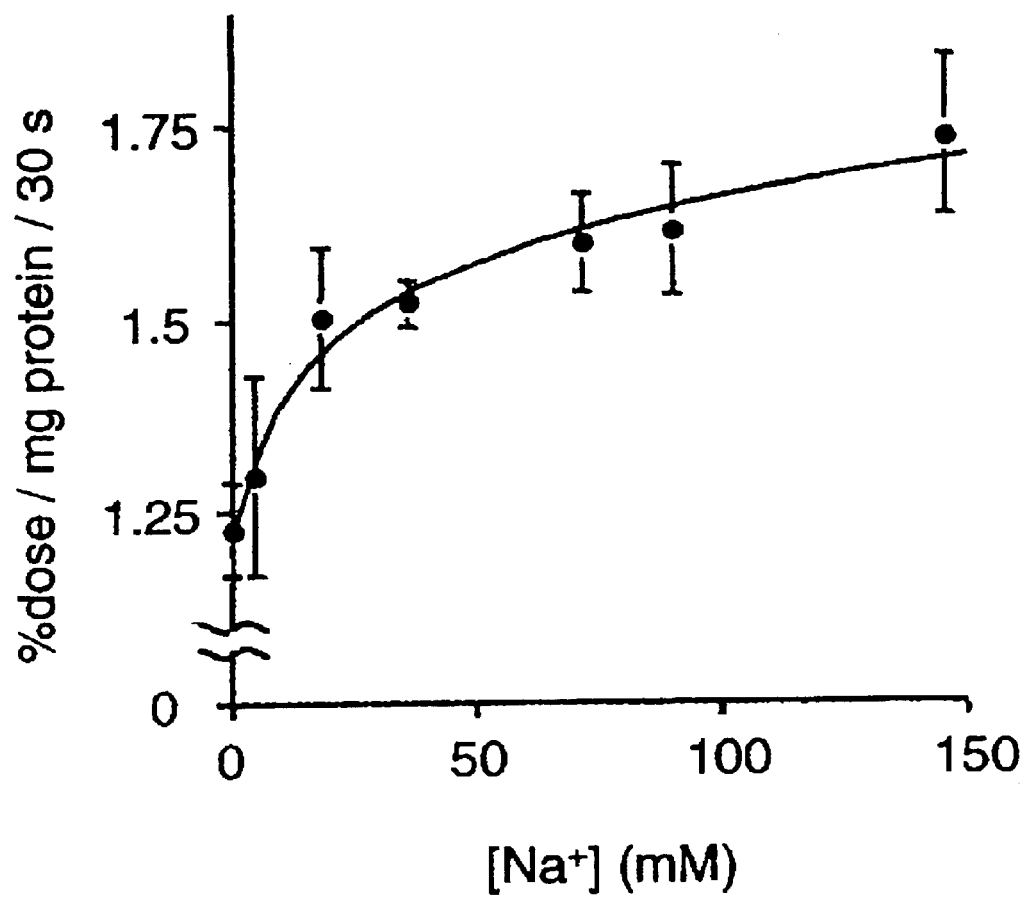
FIG. 8 is a graph showing the effect of sodium ion concentration on the cellular uptake of $^{99m}$Tc(V)-DMS by osteoclast.

Moreover, a similar experiment was carried out except that the buffer containing $^{99m}$Tc(V)-DMS was an incubation buffer of pH 7.4 with the sodium ion concentration ([Na$^+$]) adjusted in a range from 0.1 mM to 150 mM, and the incubation time for $^{99m}$Tc(V)-DMS uptake was set at 30 seconds, to measure the uptake of $^{99m}$Tc(V)-DMS into osteoclast. The results are shown in FIG. 8.

Example 6

Figure 9:
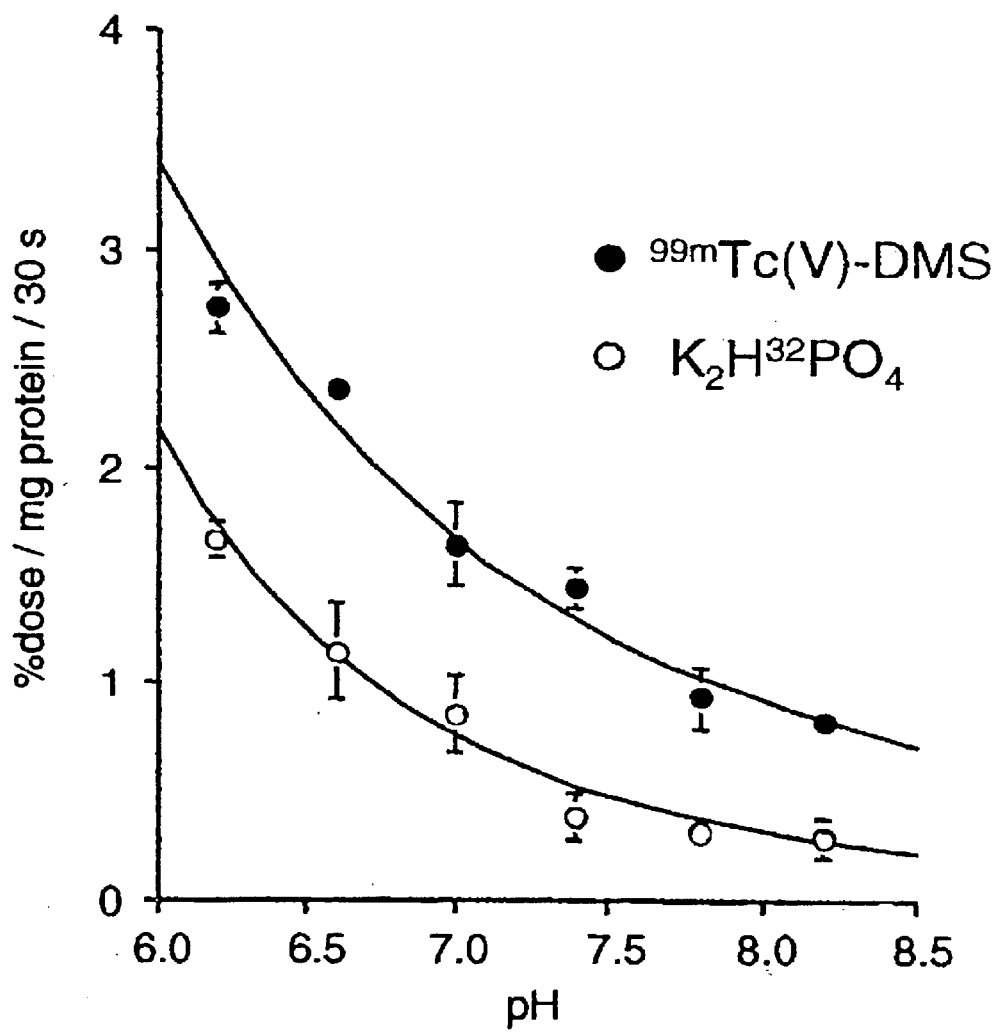
FIG. 9 is a graph showing the effect of pH on the cellular uptake of $^{99m}$Tc(V)-DMS ( ) and K$_2$H$^{32}$PO$_4$ (○) by osteoclast.

Uptake of $^{99m}$Tc(V)-DMS by Osteoclast in Comparison with K$_2$H$^{32}$PO$_4$ Effect of pH In the method described in Example 2, the pH of the incubation buffer was set at 6.2, 6.6, 7.0, 7.4, 7.8 or 8.2, and the incubation time for $^{99m}$Tc(V)-DMS uptake was set at 30 seconds, to examine effct of pH on the uptake of $^{99m}$Tc(V)-DMS into osteoclast. A similar experiment was carried out for K$_2$H$^{32}$PO$_4$, to compare the behaviors of $^{99m}$Tc(V)-DMS and K$_2$H$^{32}$PO$_4$. The results are shown in FIG. 9.

Effect of Cations

In the method described in Example 2, an incubation buffer of pH 7.4 was used for pre-incubation, and the buffer containing $^{99m}$Tc(V)-DMS was an incubation buffer of pH 7.4 containing 150 mM of sodium ions (Na$^+$), 150 mM of potassium ions (K$^+$) or 150 mM of choline, while the incubation time for $^{99m}$Tc(V)-DMS uptake was set at 30 seconds, to measure the uptake of $^{99m}$Tc(V)-DMS by osteoclast.

A similar experiment was carried out for K$_2$H$^{32}$PO$_4$, to compare the behaviors of $^{99m}$Tc(V)-DMS and K$_2$H$^{32}$PO$_4$. The results are shown in FIG. 10.

Figure 10:
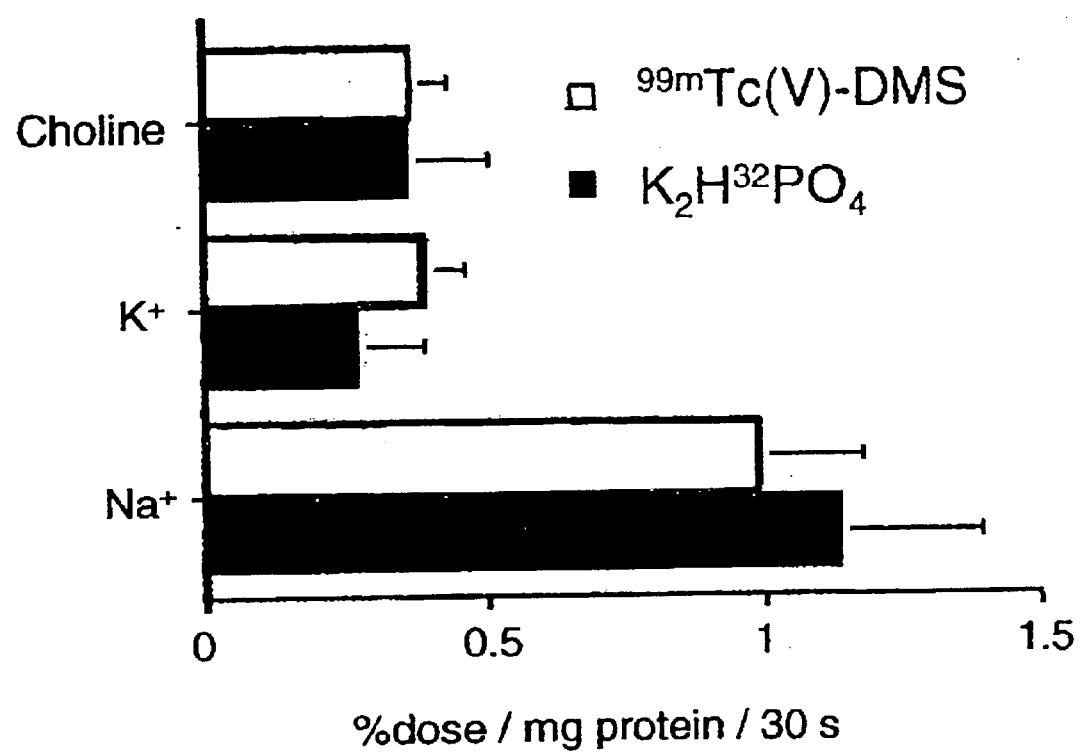
FIG. 10 is a graph showing the effect of cations on the cellular uptake of $^{99m}$Tc(V)-DMS by osteoclast.

In FIG. 10, the results are shown as values relative to the value obtained with respect to $^{99m}$Tc(V)-DMS and 150 mM of sodium ions.

The results of FIGS. 6 through 10 suggest that $^{99m}$Tc(V)-DMS shows a behavior similar to that of phosphoric acid in terms of the uptake by osteoclast, and is taken up by osteoclast through the Na$^+$-dependent phosphate transporter which relates to the inorganic phosphate transport of osteoclast.

Example 7

Uptake of $^{186}$Re(V)-DMS by Osteoclast $^{99m}$Tc is unsuitable for autoradiography since it has a half life of 6 hours and is a gamma ray-emitting nuclide. Considering this, a radioisotope of Re that is a homologous element of Tc was used to evaluate the in vivo accumulation of $^{99m}$Tc(V)-DMS in osteoclast.

$^{186}$Re(V)-DMS prepared according to a method described by Horiuchi et al. (Nucl. Med. Biol. 26: 771–779 (1999)) was administered in an amount of 370 kBq to a Wistar male rat, and the rat was sacrificed 3 hours later. Knee joints were extracted, and 30 μm thick specimens were prepared and autoradiographed. Furthermore, from the same regions, 20 μm thick specimens were prepared and the tartaric acid-resistant acidic phosphatase as an osteoclast marker or the alkaline phosphatase as an osteoblast marker was detected by means of staining. The results of the autoradiography and staining were compared to evaluate the accumulation of $^{99m}$Tc(V)-DMS in osteoclast. The results are shown in FIGS. 11 through 13.

Figure 11:
FIG. 11 is an autoradiograph of a specimen (knee joint) obtained from a rat administered with $^{186}$Re(V)-DMS in Example 7.
Figure 12:
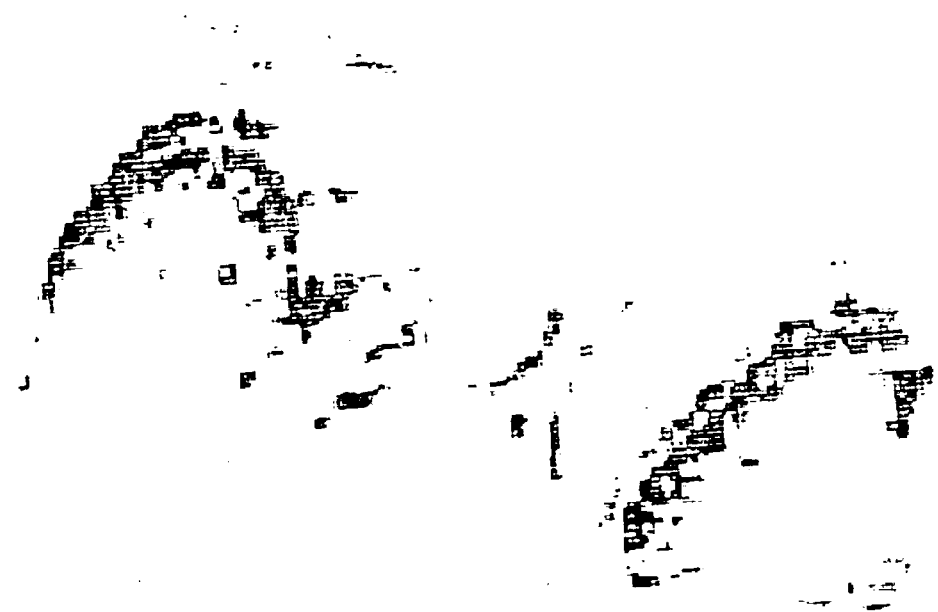
FIG. 12 is a photograph of stained tartaric acid-resistant acidic phosphatase of a specimen (knee joint) obtained from a rat administered with $^{186}$Re(V)-DMS in Example 7.
Figure 13:
FIG. 13 is a photograph of stained alkaline phosphatase of a specimen (knee joint) obtained from a rat administered with $^{186}$Re(V)-DMS in Example 7.

From FIGS. 11 through 13, it can be seen that the distribution of $^{186}$Re(V)-DMS (FIG. 11) well agrees with the distribution of osteoclast (FIG. 12), showing that the accumulation of $^{99m}$Tc(V)-DMS in osteoclast is specific.

What is claimed is:

1. A method of diagnosis for localization of osteoclast, which comprises administering a patient with a diagnostic imaging agent that contains $^{99m}$Tc(V)-dimercaptosuccinic acid as an effective ingredient, and then taking a scintigram, whereby osteoclast is located.

2. A method according to claim 1, in which the localization of osteoclast is caused by cancerous bone metastasis.

3. A method for selecting a therapy for osteoclastic type or mixed type cancerous bone metastasis for a patient in diagnosed need of such therapy, said method comprising using a diagnostic imaging agent containing $^{99m}$Tc(V)-dimercaptosuccinic acid as an effective ingredient in identifying the existence of or locating an osteoclastic type or mixed type cancerous bone metastasis to diagnose a patient in need of such therapy, said $^{99m}$Tc(V)-dimercaptosuccinic acid having preferential specificity for said osteoclastic type rather than an osteoblast type of cancerous bone metastasis; and selecting said therapy for said patient for the identified or located osteoclastic type or mixed type cancerous bone metastasis.

4. A method according to claim 3, wherein said therapy selected comprises administering to said patient a therapeutic agent comprising a bisphosphonate compound.

5. A method according to claim 4, wherein said therapeutic agent is selected from the group consisting of etidronate, clodronate, pamidronate, alendronate, ibandronate, icadronate, olpadronate, zoledronate, tiludronate, neridronate, risendronate, YH592 and EB-1053.

6. A method according to claim 3, wherein said therapy selected comprises intravenously administering a bisphosphonate compound to said patient as a bone palliation agent.

7. A method according to claim 3, wherein said therapy selected comprises intravenously administering to said patient a composition containing a member selected from the group consisting of $^{89}$SrCl$_2$, $^{186}$Re, and $^{86}$Re-labeled dimercaptosuccinic acid.

8. A method according to claim 7, wherein said therapy further comprises irradiating the cancerous bone metastasis in vivo.

9. A method according to claim 7, wherein said composition contains $^{89}$SrCl$_2$.

* * * * *